United States Patent
Ozawa et al.

(10) Patent No.: US 8,214,042 B2
(45) Date of Patent: Jul. 3, 2012

(54) TECHNIQUES FOR CONTROLLING CHARGING OF BATTERIES IN AN EXTERNAL CHARGER AND AN IMPLANTABLE MEDICAL DEVICE

(75) Inventors: Robert Dai Ozawa, Woodland Hills, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 504 days.

(21) Appl. No.: 12/471,626

(22) Filed: May 26, 2009

(65) Prior Publication Data

US 2010/0305662 A1    Dec. 2, 2010

(51) Int. Cl.
*A61N 1/378* (2006.01)
(52) U.S. Cl. ............................................. 607/29
(58) Field of Classification Search ............... 607/29, 607/30, 33
See application file for complete search history.

(56) References Cited

U.S. PATENT DOCUMENTS

| | | | |
|---|---|---|---|
| 4,014,346 A | 3/1977 | Brownlee et al. | 128/419 |
| 4,082,097 A | 4/1978 | Mann et al. | 128/419 |
| 4,096,866 A | 6/1978 | Fischell | 128/419 |
| 4,432,363 A | 2/1984 | Kakegawa | 128/419 |
| 4,903,699 A | 2/1990 | Baker, Jr. et al. | 128/419 |
| 5,184,059 A | 2/1993 | Patino et al. | 320/15 |
| 5,237,259 A | 8/1993 | Sanpei | 320/23 |
| 5,279,292 A | 1/1994 | Baumann et al. | 607/137 |
| 5,285,779 A | 2/1994 | Cameron et al. | 607/5 |
| 5,314,453 A | 5/1994 | Jeutter | 607/61 |
| 5,350,413 A | 9/1994 | Miller | 607/61 |
| 5,411,537 A | 5/1995 | Munshi et al. | 607/33 |
| 5,690,693 A | 11/1997 | Wang et al. | 607/61 |
| 5,702,431 A | 12/1997 | Wang et al. | 607/61 |

(Continued)

FOREIGN PATENT DOCUMENTS

WO    9640367    12/1996

(Continued)

OTHER PUBLICATIONS

International Search Report and Written Opinion regarding corresponding application No. PCT/US2010/034666, dated Dec. 2, 2010.

(Continued)

*Primary Examiner* — Brian T Gedeon
(74) *Attorney, Agent, or Firm* — Wong, Cabello, Lutsch, Rutherford & Brucculeri, LLP

(57) ABSTRACT

Disclosed are charging algorithms implementable in an external charger for controlling the charging of both an external battery in the external charger and an implant battery in an implantable medical device. Because full-powered simultaneous charging of both batteries can generate excessive heat in the external charger, the various charging algorithms are designed to ensure that both batteries are ultimately charged, but in a manner considerate of heat generation. In some embodiments, the charging algorithms prevent simultaneous charging of both batteries by arbitrating which battery is given charging precedence at a given point in time. In other embodiments, the charging algorithms allow for simultaneous charging of both batteries, but with at least one of the batteries being only weakly charged at low power levels. In other embodiments, the temperature generated in the external charger is monitored and used to control the charging algorithm. In these embodiments, if a safe temperature is exceeded, then the charging algorithms change to new temperature-reducing schemes which still allow for both batteries to be ultimately charged.

27 Claims, 15 Drawing Sheets

U.S. PATENT DOCUMENTS

| | | | |
|---|---|---|---|
| 5,713,936 A | 2/1998 | Staub et al. | 607/29 |
| 5,733,313 A | 3/1998 | Barreras, Sr. et al. | |
| 5,749,909 A * | 5/1998 | Schroeppel et al. | 607/33 |
| 6,198,253 B1 | 3/2001 | Kurle et al. | 320/132 |
| 6,366,809 B1 | 4/2002 | Olson et al. | 607/5 |
| 6,472,847 B2 | 10/2002 | Lundberg | 320/132 |
| 6,584,355 B2 | 6/2003 | Stessman | 607/29 |
| 6,940,255 B2 | 9/2005 | Loch | 320/132 |
| 7,177,690 B2 | 2/2007 | Woods et al. | 607/29 |
| 7,177,691 B2 * | 2/2007 | Meadows et al. | 607/36 |
| 2005/0075696 A1 | 4/2005 | Forsberg et al. | |
| 2005/0113887 A1 | 5/2005 | Bauhahn et al. | |
| 2005/0143782 A1 | 6/2005 | Stessman | 607/29 |
| 2005/0177198 A1 | 8/2005 | Norton et al. | 607/29 |
| 2005/0245983 A1 | 11/2005 | Kast et al. | 607/36 |
| 2005/0275382 A1 | 12/2005 | Stessman et al. | 320/143 |
| 2005/0288743 A1 | 12/2005 | Ahn et al. | 607/61 |
| 2006/0025829 A1 | 2/2006 | Armstrong et al. | 607/29 |
| 2006/0093894 A1 | 5/2006 | Scott et al. | 429/50 |
| 2008/0027500 A1 | 1/2008 | Chen | 607/33 |
| 2008/0097529 A1 | 4/2008 | Parramon et al. | 607/2 |
| 2009/0112291 A1 | 4/2009 | Wahlstrand et al. | 607/61 |

FOREIGN PATENT DOCUMENTS

| | | |
|---|---|---|
| WO | 9942173 | 8/1999 |
| WO | 2004010520 | 1/2004 |
| WO | 2007050657 | 5/2007 |
| WO | 2007/064609 | 6/2007 |

OTHER PUBLICATIONS

Invitation to Pay Additional Fees and, Where Applicable, Protest Fee, from the International Searching Authority regarding corresponding application No. PCT/US2010/034666, dated Jul. 27, 2010.

U.S. Appl. No. 12/354,406, filed Jan. 15, 2009, Marnfeldt et al.

U.S. Appl. No. 12/368,385, filed Feb. 10, 2009, Aghassian.

* cited by examiner

US 8,214,042 B2

TECHNIQUES FOR CONTROLLING CHARGING OF BATTERIES IN AN EXTERNAL CHARGER AND AN IMPLANTABLE MEDICAL DEVICE

FIELD OF THE INVENTION

The present invention relates generally to implantable medical device systems, and in particular to systems employing an external charger apparatus.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder sublaxation, etc. Implantable stimulation devices may comprise a microstimulator device of the type disclosed in U.S. Patent Application Publication 2008/0097529, or larger types of stimulators such as spinal cord stimulators or pacemakers for example.

Microstimulator devices typically comprise a small, generally-cylindrical housing which carries electrodes for producing a desired electric stimulation current. Devices of this type are implanted proximate to the target tissue to allow the stimulation current to stimulate the target tissue to provide therapy. A microstimulator's case is usually on the order of a few millimeters in diameter by several millimeters to a few centimeters in length, and usually includes or carries stimulating electrodes intended to contact the patient's tissue. However, a microstimulator may also or instead have electrodes coupled to the body of the device via a lead or leads. A multi-electrode microstimulator 10 having a single anode (Ea) and several selectable cathodes (Ec1 et seq.) in shown in FIG. 1. Further details regarding such a microstimulator 10 can be found in the above-referenced '529 application.

Implantable microstimulators 10 are typically powered by an internal battery, which periodically needs to be recharged. Such recharging is usually accomplished by an external charger, which produces a magnetic field to ultimately induce a current in a coil in the implant. This induced current is rectified, and used to charge the implant battery.

Recharging the implant battery by magnetic induction works well, and allows the implant battery to be charged wirelessly and transcutaneously (i.e., through the patient's tissue). However, such techniques also suffer from heat generation. In particular, the external charger can heat up, and if it gets too hot may burn the patient.

The inventors have noted that this problem of external charger overheating can be exacerbated if the external charger itself requires recharging. In this regard, note that the external charger may too contain a rechargeable battery, whose power is used to produce the magnetic field to charge the implant's battery. If the external charger's battery needs recharging, this provides an additional heat load on the external charger, particularly if the external charger's battery and the implant's battery require recharging at the same time. The inventors believe that a solution to this problem of excessive heating in an external charger is therefore indicated, and this disclosure provides solutions.

DETAILED DESCRIPTION

Disclosed are charging algorithms implementable in an external charger for controlling the charging of both an external battery in the external charger and an implant battery in an implantable medical device. Because full-powered simultaneous charging of both batteries can generate excessive heat in the external charger, the various charging algorithms are designed to ensure that both batteries are ultimately charged, but in a manner considerate of heat generation. In some embodiments, the charging algorithms prevent simultaneous charging of both batteries by arbitrating which battery is given charging precedence at a given point in time. In other embodiments, the charging algorithms allow for simultaneous charging of both batteries, but with at least one of the batteries being only weakly charged at low power levels. In other embodiments, the temperature generated in the external charger is monitored and used to control the charging algorithm. In these embodiments, if a safe temperature is exceeded, then the charging algorithms change to new temperature-reducing schemes which still allow for both batteries to be ultimately charged.

Figure 1:
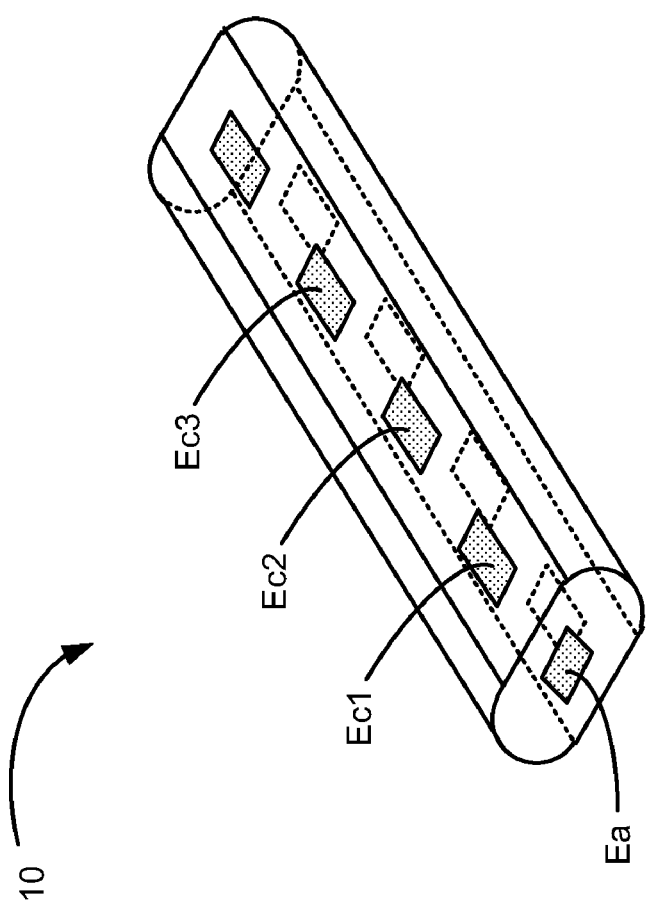
FIG. 1 illustrates a microstimulator device of the prior art.
Figure 2:
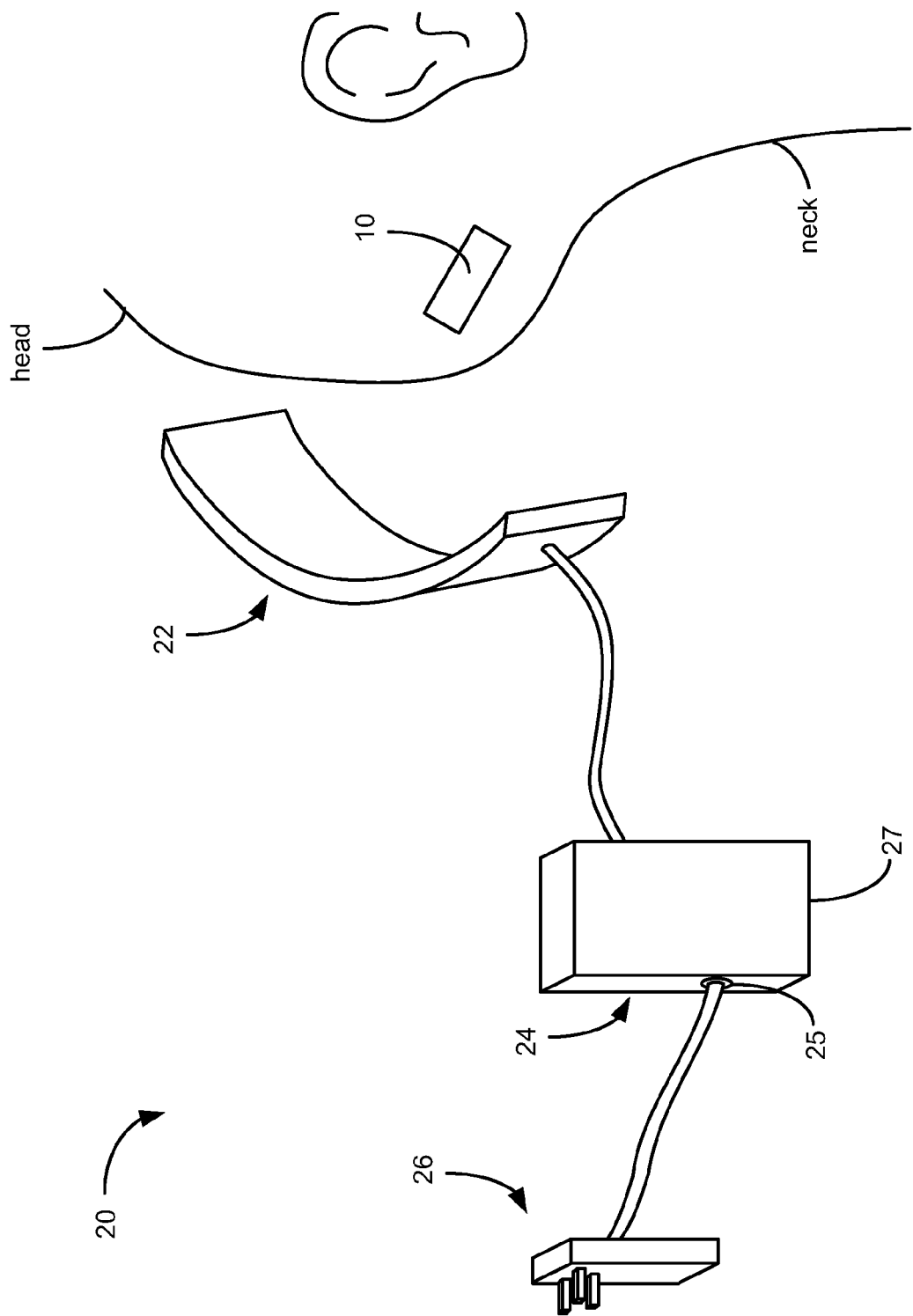
FIG. 2 illustrates the microstimulator of FIG. 1 as implanted, and shows external charging components used for charging a battery in the microstimulator.

FIG. 2 shows a microstimulator 10 as implanted in a patient. In the illustrated application, the microstimulator 10 is implanted within the head of a patient, although this is merely exemplary and could be implanted elsewhere. When implanted in the head, the microstimulator 10 can be used to stimulate the occipital nerves, which can be beneficial in the treatment of migraine headaches for example. More than one microstimulator 10 may be implanted, but only one is shown for convenience.

Figure 3A:
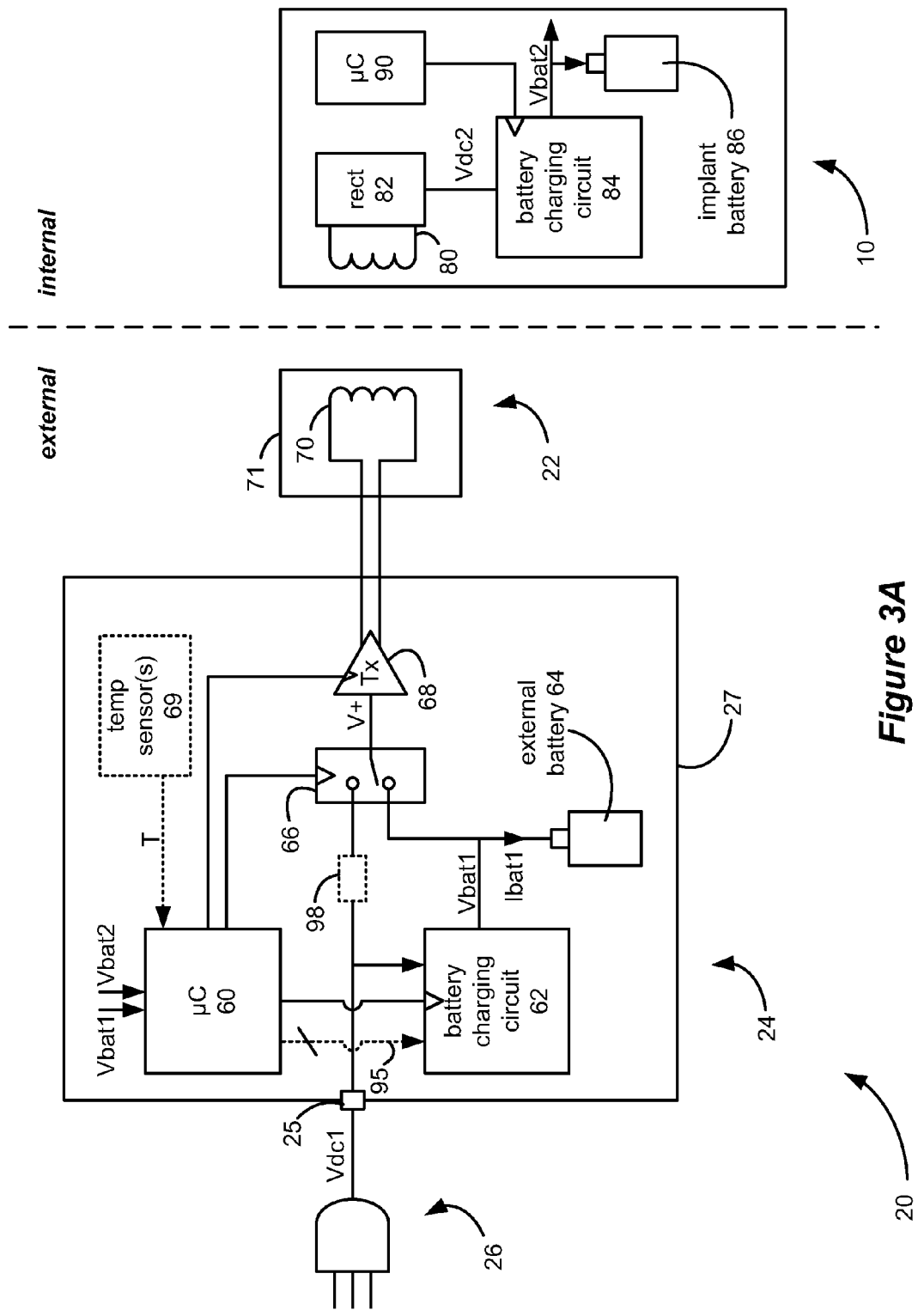
FIGS. 3A and 3B illustrate circuitry useable in the external charging components to implement the disclosed charging algorithms that regulate charging of both an external battery in the external charging components and an implant battery in the microstimulator.
Figure 3B:
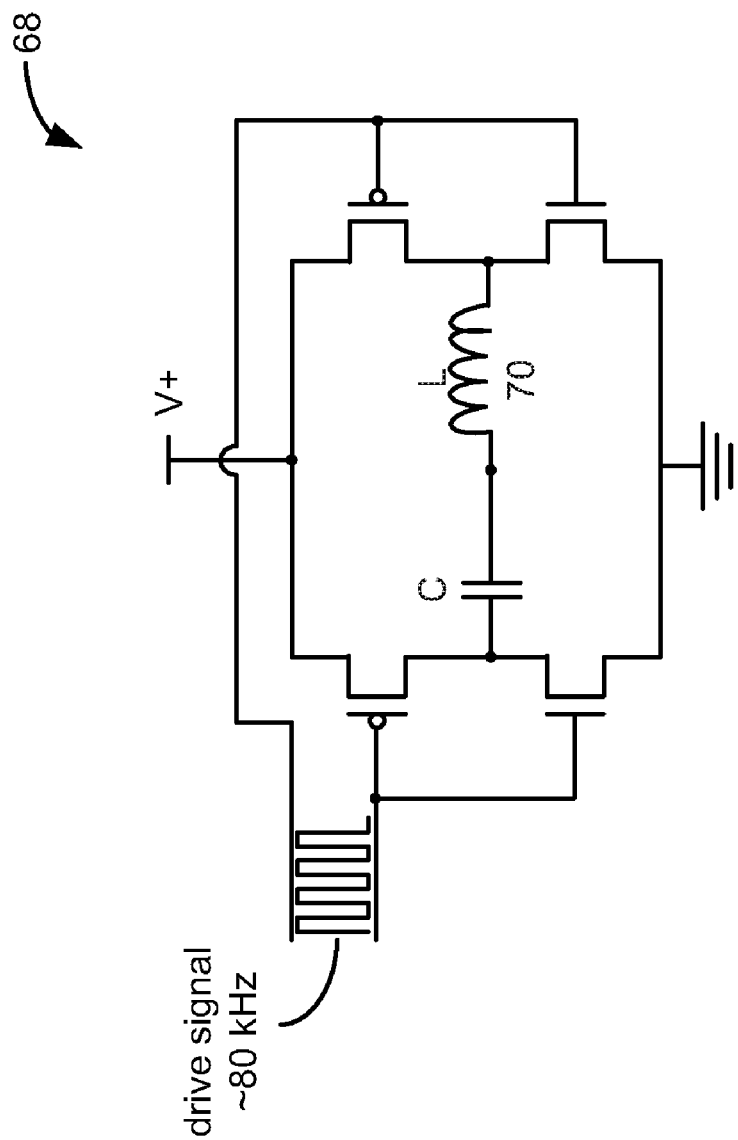

Also shown in FIG. 2 are various external charging components 20, the circuitry details of which are shown in FIGS. 3A and 3B. The basic function of the external charging components 20 is to wirelessly recharge an implant battery 86 in the microstimulator 10. The implant battery 86 provides the power for the microstimulator 10, including the circuits that ultimately provide therapeutic pulses to the microstimulator's electrodes. The external charging components 20 can be used to recharge the implant battery 86 as needed, perhaps on a daily basis. Together, the external charging components 20 can be referred to as the external charger.

The external charging components 20 comprise a head piece 22 and a coil controller 24. As shown in FIG. 3A, the head piece 22 comprises a coil 70 covered or encapsulated in a cover 71. The cover 71 is shaped to be comfortably held in place on the back of the head near the site at which the microstimulator(s) 10 is implanted, and may include a head band for example. When energized, coil 70 produces a magnetic charging field, which is received transcutaneously (i.e., through the patient's tissues) at a charging coil 80 within the microstimulator 10. The current induced in the charging coil 80 is rectified (82) to a suitable DC level (Vdc2) and charges the implant battery 86, perhaps using a battery charging circuit 84 as an intermediary. The implant battery will be deemed sufficiently charged when its voltage exceeds some pre-determined level, e.g., voltage threshold Vt2 as will be discussed in further detail below.

As its name implies, the coil controller 24 controls the charging coil 70 in the head piece 22, and contains a wireless transmitter 68, which is used to drive the coil 70 to produce the necessary magnetic charging field. The transmitter 68 creates an alternating current across the coil 70, and can comprise a resonant circuit such as an inductor-capacitor (L-C) tank circuit, as shown in FIG. 3B. The drive signal to the tank circuit sets the frequency of the produced wireless magnetic charging field, which might be in the neighborhood of 80 kHz for example. Transistor switches allow the tank circuit's power supply, V+, to be placed across the L-C series circuit with alternating polarities. Further details concerning this type of tank circuit can be found in U.S. patent application Ser. No. 12/368,385, filed Feb. 10, 2009. The transmitter 68 is controlled by a microcontroller 60 within the coil controller 24. The coil controller 24 contains other electronics which will be discussed in further detail later. Such coil controller 24 electronics can be placed inside a plastic housing 27 for example, which housing may carry a user interface (e.g., an on/off button, input buttons, LEDs, a display, speakers, etc.) if desired.

External charging components 20 also include a plug 26 for tapping into an AC power source such as a wall outlet or other source. The plug 26 includes transformer and rectifier circuitry not shown, and so provides power to the coil controller 24 in the form of a DC voltage, Vdc1. However, such transformer and rectifier circuitry can also exist in the housing 27 of the coil controller itself, although this is not shown for convenience. Plug 26 can be coupled to the coil controller at connector 25.

Coil controller 24 includes a rechargeable external battery 64, which can be recharged using the DC voltage, Vdc1, provided by the plug 26. To regulate the charging current (Ibat1) and otherwise protect the external battery 64, battery charging circuitry 62 is used. Such battery circuitry 62 is commercially available in the art, and may comprise product LT4002 from Linear Technology for example. Battery circuitry 62 is controlled by microcontroller 60. Like the implant battery 86, the external battery 64 in the coil controller 24 will be deemed sufficiently charged when its voltage exceeds some threshold, e.g., Vt1 as discussed further below.

After the external battery 64 is recharged, the plug 26 can be disconnected from connector 25 on the coil controller 24. This allows the coil controller 24 to be used without being tethered to a wall socket for example, which allows a patient wishing to recharge the internal battery 86 in her microstimulator 10 "on the go". When disconnected from the plug 26, the coil controller 24 receives it operating power exclusively from the external battery 64, Vbat1, which would be used to power the controller's electronics and (most significantly from a power consumption standpoint) the transmitter 68 used to energize coil 70. Powering of the transmitter 68, i.e., provision of the power supply voltage V+ to be applied to the transmitter's tank circuit, occurs via a switch 66 operating under control of the microcontroller 60.

Although the coil controller 24 can be decoupled from the plug 26, they would be connected when charging the external battery 64, or when charging the external battery 64 and the implant battery 86 at the same time. When plug 26 is coupled to the coil controller 24, either the voltage from the plug (Vdc1), or the voltage of the external battery 64 (Vbat1) depending on its level of depletion, can be used to provide power to the transmitter 68. Switch 66 controls whether Vdc1 or Vbat1 is chosen as the power source V+ for the transmitter 68. (Optional regulator 98 is ignored for now, but will be discussed later).

Before discussing the various manners in which the external charging components 20 can be used in accordance with embodiments of the invention, various portions of the external charging components 20 could be integrated. For example, while it is convenient to separate the coil 70 in the head piece 22 from the coil controller 24 for the occipital nerve stimulation application illustrated in FIG. 2, such separation is not necessary. In a spinal cord stimulator application for instance, the coil 70 could be integrated within housing 27 of the coil controller 24, such as is shown in U.S. Patent Publication 2008/0027500 for example.

As noted in the Background, operation of the external charging components 20 to recharge the implant battery 86 can cause heating. In particular, the inventors have noticed that the transmitter circuit 68 in the coil controller 24 is subject to heating during creation of the magnetic charging field. The inventors have also noticed that additional heat can be generated in the coil controller 24 if the external battery 64 too requires charging, i.e., if the coil controller is coupled to the plug 26 and the battery charging circuitry 62 is activated to charge the external battery 64. The battery charging circuitry 62 provides a significant source of additional heating. When heat from the battery charging circuitry 62 is combined with heat from the transmitter circuitry 68, the coil controller 24 can get excessively hot. Because the coil controller 24 can be held against a patient's skin using a restraining belt for example, the risk of injury during simultaneous charging of the external battery 64 and the implant battery 86 is problematic.

FIGS. 4-11 disclose various charging algorithms in which implant battery charging and external battery charging are controlled to prevent overheating the coil controller 24. Each disclosed algorithm can be designed to automatically run, for example: when the patient selects to charge the implant battery 86 via a selection made on the coil controller 24's user interface (not shown); when the coil controller 24 is turned on; when the coil controller 24 is plugged into an AC power source using plug 26; or upon the occurrence of any other condition in which it is logical or necessary to charge either or both of the implant battery 86 or the external battery 64 in the coil controller 24. One skilled in the art will understand that the disclosed algorithms can be implemented by the microcontroller 60 in the coil controller 24.

A group of steps 100 define example initial conditions which set the stage for implementation of the invention, which steps 100 are essentially geared to determining whether charging of both the implant battery 86 in the microstimulator 10 and the external battery 64 in the coil controller 24 is warranted and possible. Because these initial steps can be the same for each of the disclosed embodiments of FIGS. 4-11, they are repeated at the beginning of those figures. However, these initial steps 100 are merely illustrative, and could be deleted, altered, or added to in useful implementations.

As a first initial step, the microcontroller 60 in the coil controller 24 determines if it is coupled via plug 26 to an external power source such as a wall socket, which determination can be made by assessing whether the Vdc1 is present. If not, the external battery 64 cannot be charged, and if necessary, the implant battery 86 can be charged. Because Vdc1 is not present, switch 66 would route the external battery voltage, Vbat1, to the transmitter 68's power supply V+. If the external battery 64 is sufficient to produce a magnetic charging field, then charging of the implant battery 86 can commence as normal; if not sufficient, then charging would terminate in typical fashion.

If the coil controller 24 is plugged in and Vdc1 is present, next initial steps 100 ask whether either or both of the external battery 64 or the implant battery 86 require charging. This can comprise assessing whether the voltage of those batteries 64 and 86, i.e., Vbat1 and Vbat2 respectively, is below some capacity threshold voltage, i.e., Vt1 and Vt2 respectively. Of course, other methods exist for determining battery capacity, and comparison to a threshold voltage should be understood as merely exemplary.

Determining the voltage of external battery 64, Vbat1, is straight forward for the microcontroller 60 in the coil controller 24, because the external battery is within the controller; any well known analog-to-digital or comparator circuitry can be used determine Vbat1 and/or its relation to threshold Vt1. Determination of the voltage of the implant battery 86, Vbat2, requires similar measuring circuitry at the microstimulator 10, and telemetry of the determined Vbat2 value to the coil controller 24. Such telemetry can occur using load shift keying, in which the impedance of charging coil 80 in the microstimulator 10 is modulated with the battery voltage data, causing detectable reflections in the active transmitter coil 70. Such a means of back telemetry from the microstimulator 10 to the external charging coil 70 is well known and is discussed further in U.S. patent application Ser. No. 12/354,406, filed Jan. 15, 2009.

If the implant battery 86 does not require charging (i.e., Vbat2>Vt2) but the external battery 64 requires charging (Vbat1<Vt1), then the external battery is charged using Vdc1. Specifically, the battery charging circuitry 62 is enabled and the transmitter 68 is disabled by the microcontroller 60. Because the transmitter 68 is disabled, the position of switch 66 does not matter.

By contrast, if the implant battery 86 requires charging (i.e., Vbat2<Vt2) but the external battery 64 does not require charging (Vbat1>Vt1), then the implant battery is charged using Vbat1. Specifically, the battery charging circuitry 62 is disabled, and the transmitter 68 is enabled. In this condition, both Vbat1 and Vdc1 are present, and either could be passed by the switch 66 to power the transmitter 68 (V+). However, it can be preferable for switch 66 to apply the external battery voltage, Vbat1, to the transmitter. This is because the transmitter 68 and coil 70 are normally optimized to work in a non-tethered environment in which the coil controller 24 is portable and not plugged in, such that power to energize the coil 70 can come only from the external battery 64. However, this is not strictly required, and any power supply (including Vdc1) can be used to power the transmitter 68 to produce the magnetic charging field for the implant battery 86.

If it is determined that both the implant battery 86 and the external battery 64 require charging (i.e., Vbat2<Vt2 and Vbat1<Vt1), then the algorithm exits initial steps 100 and begins steps designed to eventually charge both batteries in a manner considerate of heat generation in the coil controller 24.

Figure 4:
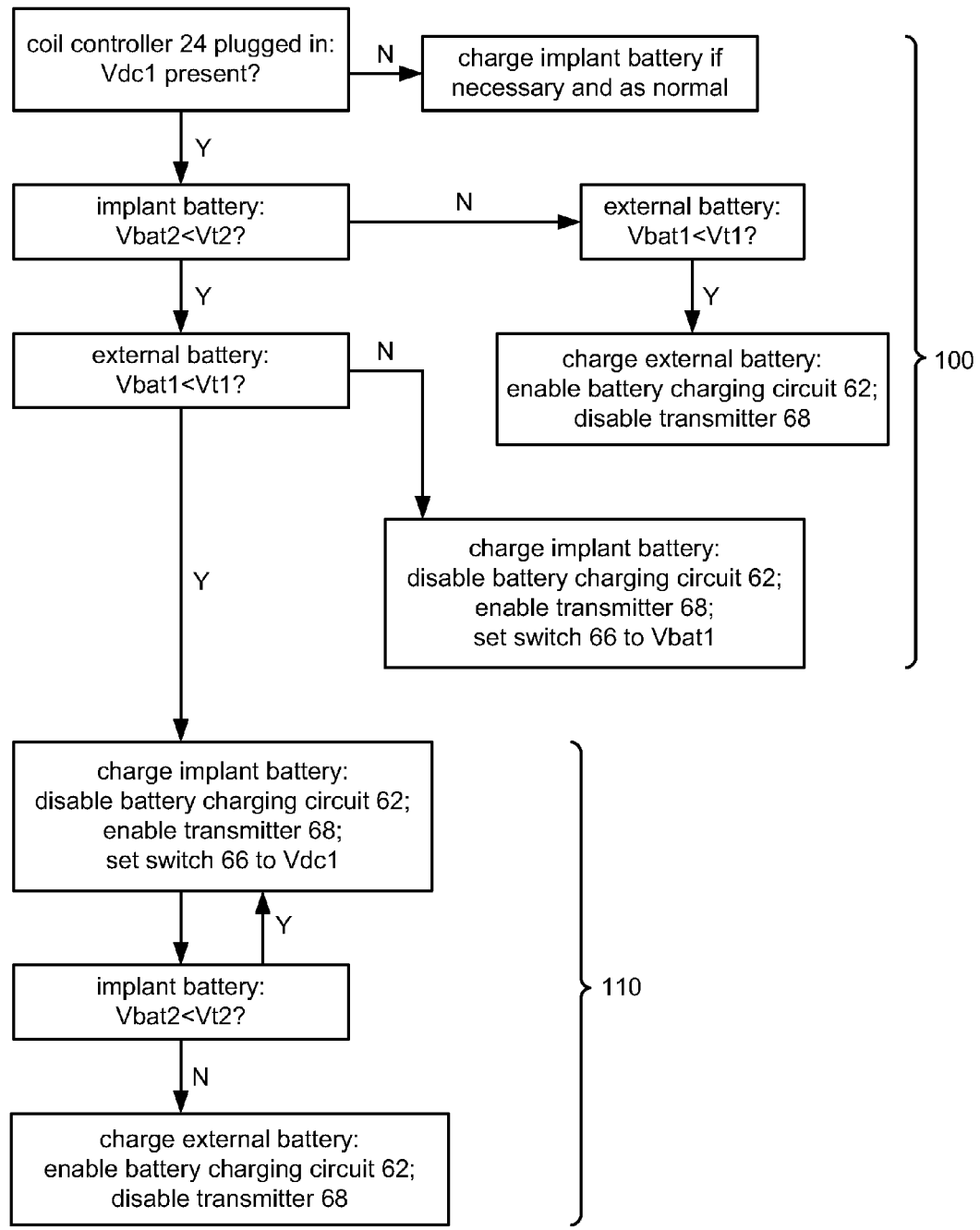
FIGS. 4 and 5 illustrate charging algorithms that charge one of the external or implant batteries first, and then the other.

In steps 110 of FIG. 4, although both the external battery 64 and the implant battery 86 require charging, charging of the implant battery 62 is given precedence, and charging of the external battery 64 does not commence until the implant battery 62 is fully charged. Therefore, the transmitter 68 is enabled by the microcontroller 60 in the coil controller 24 to produce a magnetic charging field for charging the implant battery 86. Because the external battery voltage Vbat1 is insufficient (<Vt1), the power provided to the transmitter 68 from switch 66 comprises the rectified voltage, Vdc1, from plug 26. As mentioned earlier, this may not be optimally efficient for the transmitter 68 and coil 70, which are generally tuned to operate at a fully charged external battery voltage (i.e., Vbat1=Vt1). Still, charging with Vdc1 (or some regulated version thereof, not shown), will still be sufficient under the circumstance, even if not optimal. Because precedence is initially given to charging of the implant battery 86, the battery charging circuit 62 for external battery 64 is automatically disabled by the microcontroller 60.

After some time, and preferably on a periodic basis, the implant battery voltage, Vbat2, is telemetered to the coil controller 24 in the manner discussed previously, and is assessed relatively to its threshold, Vt2. If Vbat2 is still less than its threshold Vt2, then charging of the implant battery 86 continues in the manner just discussed. However, when the implant battery 86 becomes sufficiently charged (Vbat2>Vt2), then charging of the implant battery 86 can cease, and charging of the external battery 64 can begin. Microcontroller 60 affects this by automatically enabling the battery charging circuit 62 in the coil controller and disabling the transmitter 68. This allows Vdc1 to be used to charge the external battery 64.

By the practice of steps 110, notice that the battery charging circuitry 62 and the transmitter 68 are not simultaneously enabled, even though the conditions of their respective batteries 64 and 86 might otherwise suggest that such simultaneity is warranted. Controlling two of the main heat sources in the coil controller 24 in this fashion reduces the likelihood that the coil controller 24 will overheat. As noted earlier, this improves patient safety.

Figure 5:
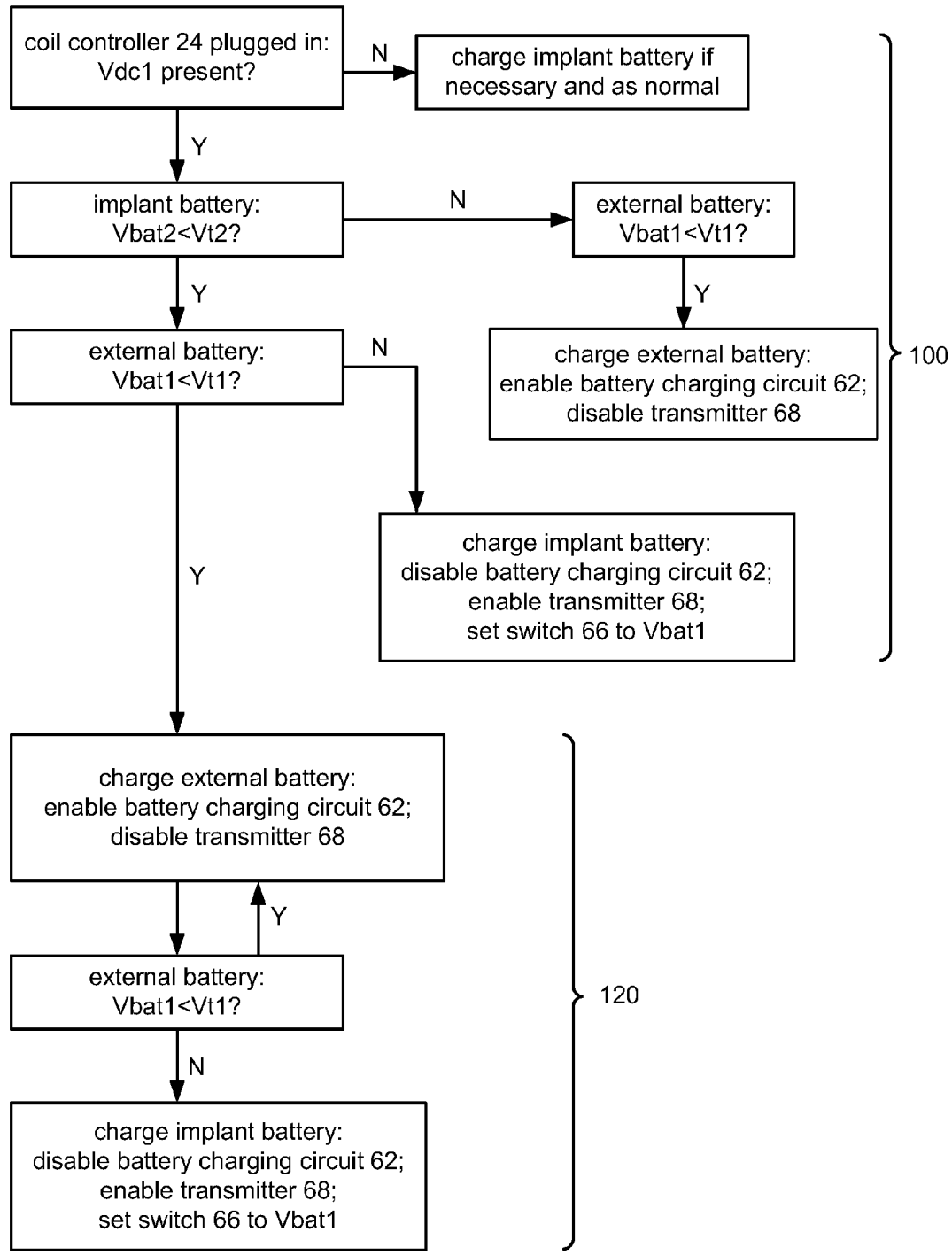

Steps 120 in FIG. 5 are similar to steps 110 in FIG. 4, except that precedence is given to charging the external battery 64. Thus, even though both batteries 64 and 86 require charging, steps 120 start by enabling the battery charging circuitry 62 to charge external battery 64 using Vdc1. The transmitter 68 is disabled to prevent generation of a magnetic charging field and charging of the implant battery 86. The voltage of the external battery, Vbat1, is checked on a periodic basis. If that voltage is less than its threshold (i.e., Vbat1<Vt1), then charging of the external battery 64 continues. Eventually, when the external battery voltage exceeds its threshold (i.e., Vbat1>Vt1), then the implant battery 86 is charged, and the external battery 64 is prevented from further charging: specifically, the transmitter 68 is enabled, and the battery charging circuitry 62 is disabled. Because the external battery 64 is sufficiently charged before charging of the implant battery 86, switch 66 preferably passes the external battery voltage, Vbat1, to the enabled transmitter 68. Again, this is preferred as an optimal match to the transmitter 68 and coil 70, but is not strictly necessary, as the enabled transmitter 68 may also be power by Vdc1, a regulated version thereof, or any other power source. Regardless, steps 120 again prevent simultaneous enablement of two primary heat sources in the coil controller 24—battery charging circuit 62 and transmitter 68—thus reducing heat and improving patient safety.

Figure 6A:
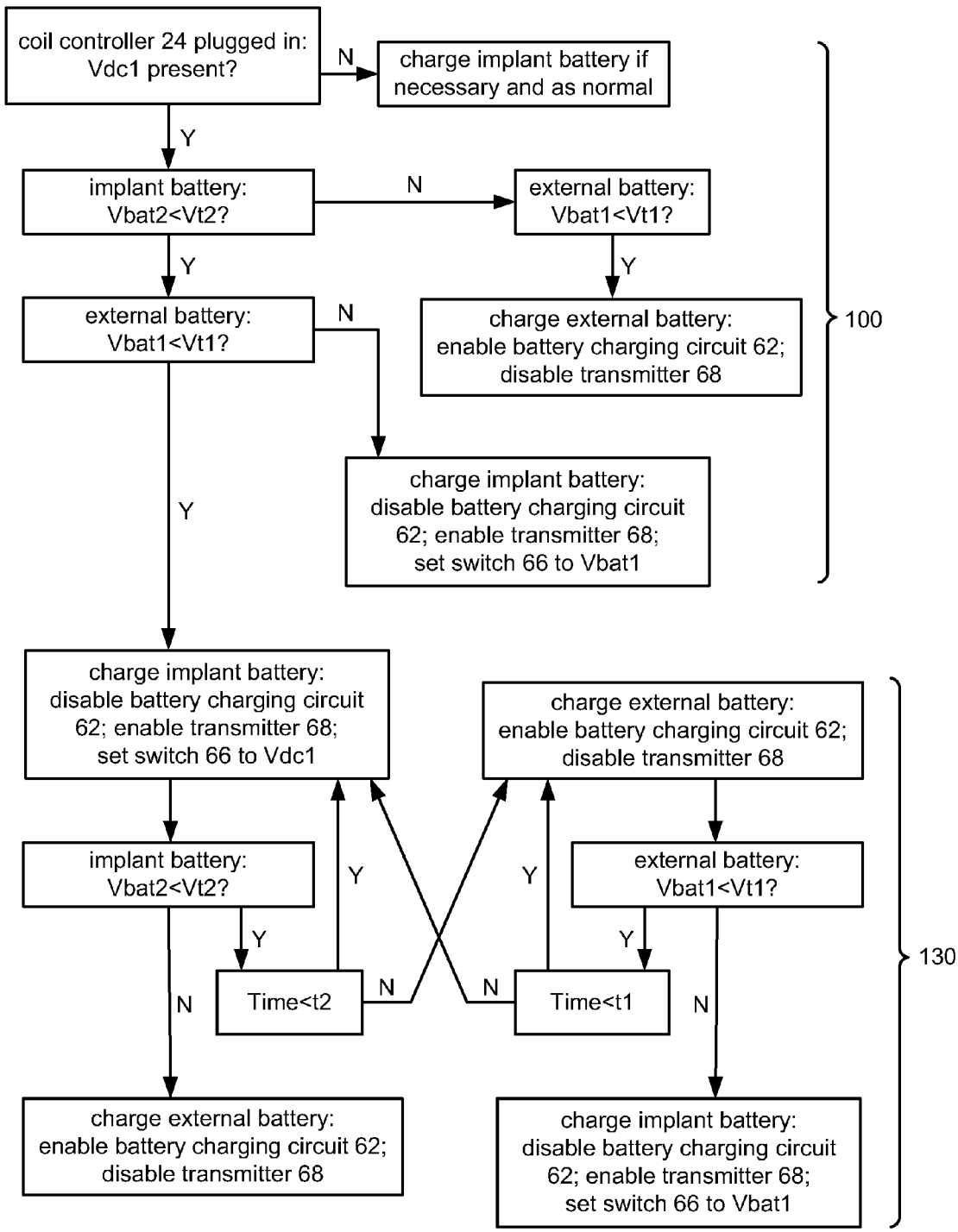
FIGS. 6A and 6B illustrate a charging algorithm that alternates between charging the external battery and the implant battery.

Steps 130 in FIG. 6A similarly prevent the simultaneous activation of these two heat sources, but do so by enabling them in an alternating fashion, such that one of the batteries 64 and 86 is charged for a time period, then the other for a time period, then the first again, then the other again, etc.

Figure 6B:
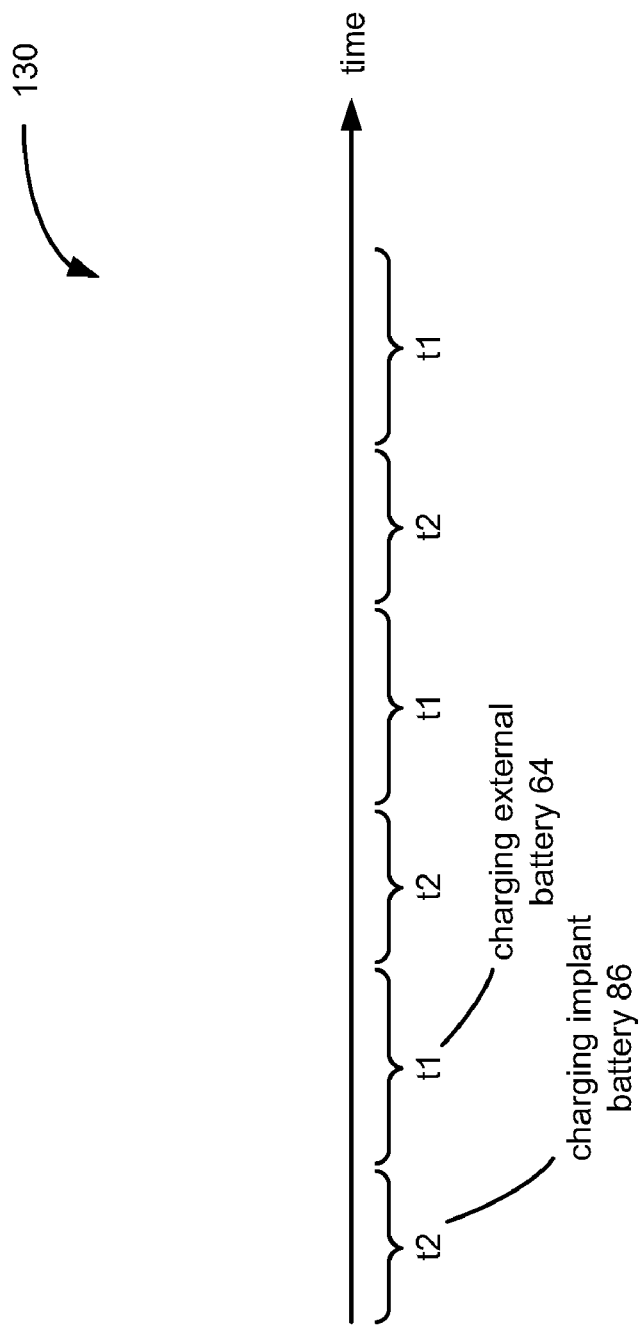

As illustrated, upon leaving initial steps 100, the implant battery 86 is charged first by disabling the battery charging circuitry 62 and enabling transmitter 68. Again, because the external battery 64 at this point is insufficiently charged, switch 66 provides Vdc1 instead to power the transmitter 68. Such charging of the implant battery 86 occurs for a time period t2, which may be set by the designers of the external charging components 20, and which may comprise 60 seconds for example. Once time t2 is exceeded, and assuming that the implant battery 86 is still undercharged (Vbat2<Vt2), then the external battery 64 is charged. This occurs by enabling the battery charging circuitry 62 and disabling the transmitter 68, which allows Vdc1 to charge the external battery 64. Charging of the external battery 64 continues in this fashion until the expiration of another time period t1. (t1 may equal t2). If after t1, the external battery 64 remains insufficiently charged (Vbat1<Vt1), then the implant battery 86 is once again charge for its time t2, etc. Such interleaving of the charging of the two batteries 64 and 86 is shown in FIG. 6B.

This back-and-forth process continues until either the external battery 64 or the implant battery 86 achieves a suitable charge, i.e., until either Vbat1>Vt1 or Vbat2>Vt2. When either of these conditions occurs, the suitably charged battery is disconnected, and the not-yet-fully charged battery is given precedence by the coil controller 24, as shown by the steps at the bottom of FIG. 6A. For example, if it is determined that the implant battery 86 is fully charged (Vbat2>Vt2), then battery charging circuit 62 is enabled, and transmitter 68 is disabled, as shown at the bottom left of FIG. 6A. This curtails charging of the implant battery 86, and allows the external battery 64 to be charged without interruption until complete (i.e., until Vbat1>Vt1). By contrast, if it is determined that the external battery 64 is fully charged (Vbat1>Vt1), then battery charging circuit 62 is disabled, and transmitter 68 is enabled, as shown at the bottom right of FIG. 6A. This curtails charging of the external battery 64, and allows the implant battery 86 to be charged without interruption until complete (i.e., until Vbat2>Vt2).

Figure 7A:
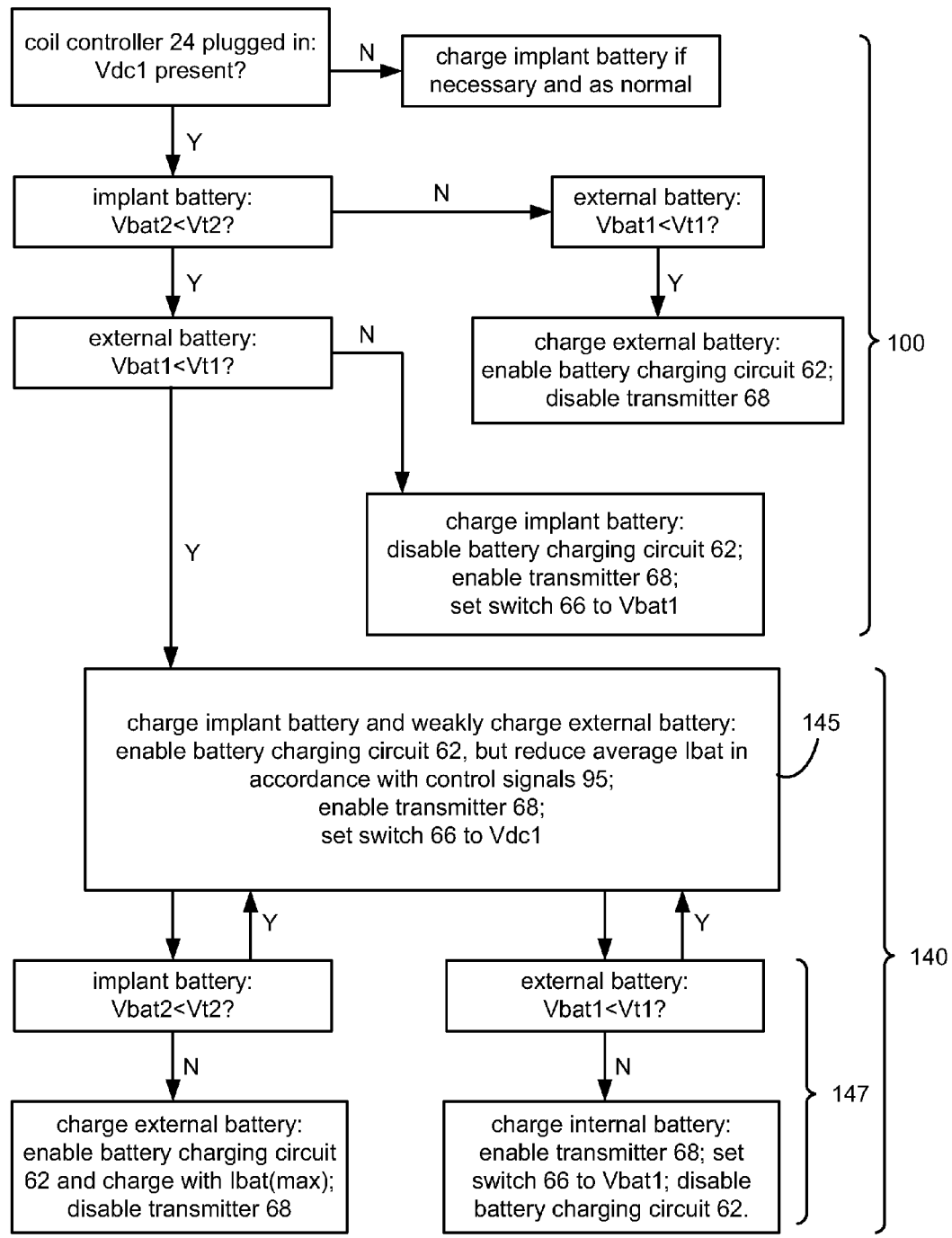
FIGS. 7A-8B illustrates charging algorithms that allow for simultaneous charging of the external and implant batteries, but only allows one of those batteries to be weakly charged at low power.
Figure 8A:
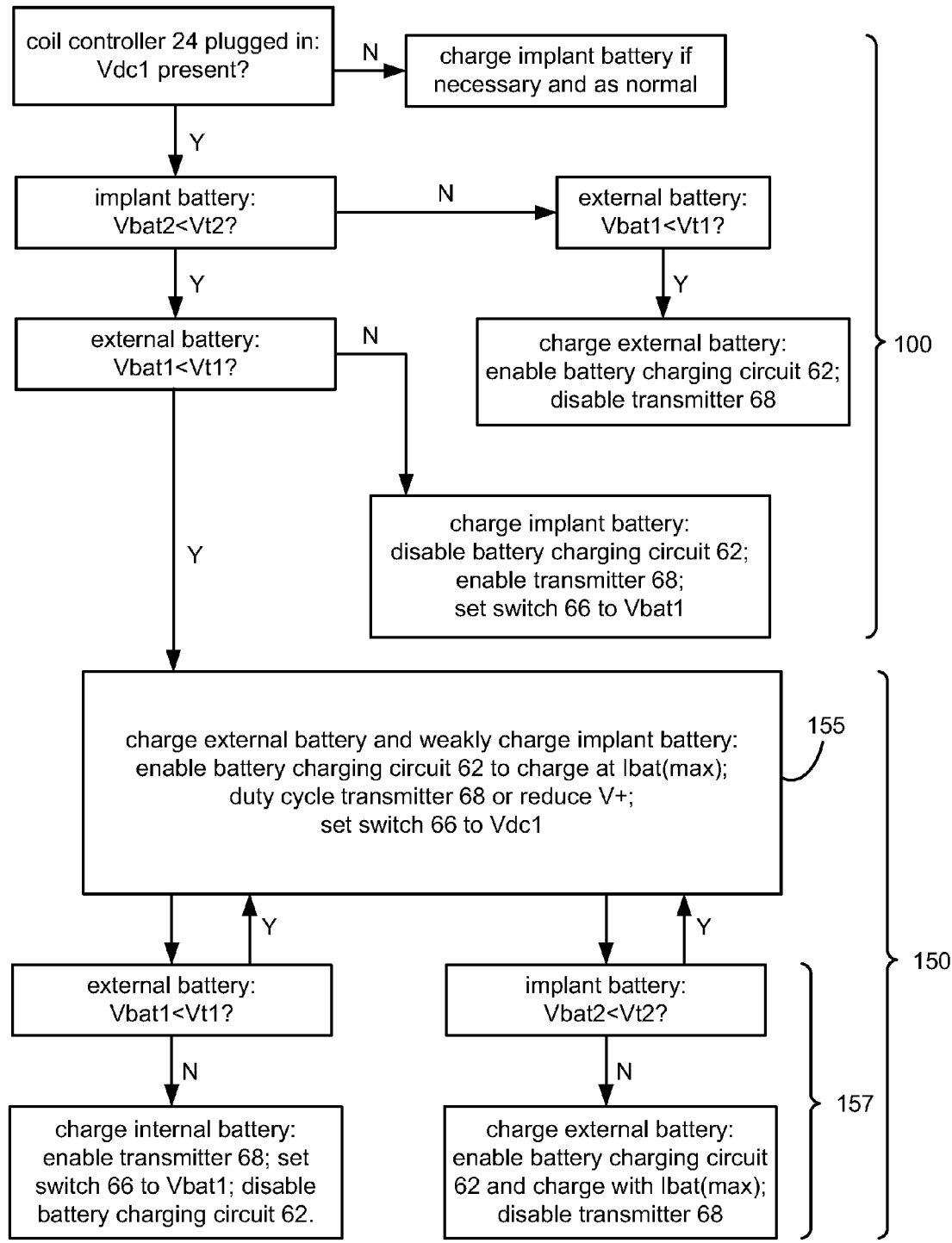

The embodiments disclosed in steps 140 in FIG. 7A and steps 150 in FIG. 8A also reduce heat generation in the coil controller 24 in the event that both the external battery 64 and the implant battery 86 require recharging. However, unlike previous embodiments, steps 140 and 150 permit simultaneous charging of both batteries 64 and 86. However, one of the batteries in steps 140 and 150 is not charged to a full extent. Instead, such one battery is only "weakly" charged, i.e., charged with a power less than would be indicated were that one battery to be charged by itself. As a result, the average power level drawn by the combination of the battery charger circuit 62 and the transmitter 68 is reduced when compared to the average power level used when both batteries are fully charged together.

In the embodiment illustrated in FIG. 7A, after performance of the initial steps 100 which determine that both batteries 64 and 86 require charging, a first step 145 provides full charging power to the implant battery 86, but at the same time also allows for weak charging of the external battery 64. Full charging of the implant battery 86, as in earlier embodiments, entails enabling the transmitter 68, and setting the switch 66 to Vdc1.

Figure 7B:
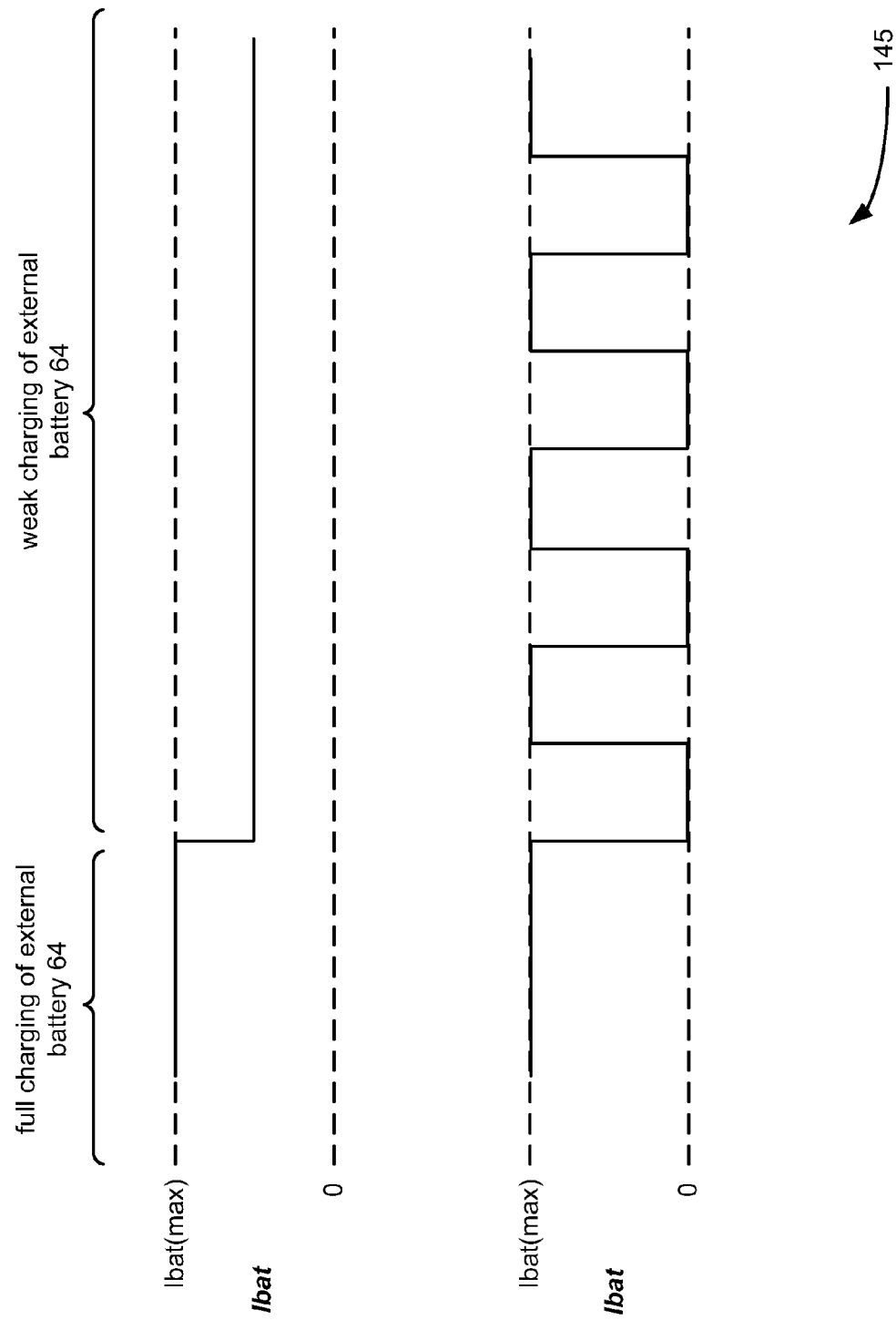

Simultaneous weak charging of the external battery 64 in step 145 can be accomplished in different ways, a couple of which are illustrated in FIG. 7B. Each of the illustrated ways involve controlling the external battery charging current, Ibat, to an average that is less than its maximum, Ibat(max), where Ibat(max) denotes the current that is normally used to fully charging the external battery 64. In the first way illustrated at the top of FIG. 7B, weak charging involves merely lowering the external battery charging current from its maximum value, e.g., to perhaps one-half of Ibat(max). In the second way illustrated at the bottom, the external battery charging current is made to duty cycle between Ibat(max) and 0; in this simple example, the average Ibat current would again be approximately one-half Ibat(max). In either case, the average power level used to charge the external battery is reduced compared to the power levels used when that battery is charged by itself. Control of the external battery charging current Ibat is performed by the battery charging circuit 62 under control of the microcontroller 60. Such control can come in the form of optimal control signal(s) 95 (FIG. 3) between the microcontroller 60 and the battery charging circuit 62, which signal(s) 95 can specify full charging or some relative amount of weak charging, etc.

During simultaneous charging of the external battery 64 and the implant battery 86, the capacities of these batteries are periodically checked. If neither is fully charged, the just-described simultaneous charging of step 145 continues. If the implant battery become fully charged first, i.e., if Vbat2>Vt2, as might be expected because it is given full-charging precedence by step 145, then charging of the implant battery 86 ceases: transmitter 68 is disabled. At this point, charging of the external battery 64 can occur as normal, i.e., with a full charging current Ibat(max) as indicated by signal 195 (FIG. 3). If the external battery 64 becomes fully charged first, i.e., if Vbat1>Vt1, then charging of the external battery 64 ceases, and charging of the internal battery 86 continues: battery charging circuit 62 is disabled, and transmitter 68 continues to be enabled. Because the external battery 64 is now charged, switch 66 can pass that battery's voltage, Vbat1, to the transmitter 68, which as indicated earlier, is preferable from a tuning standpoint.

Steps 150 in FIG. 8A are similar to steps 140 in FIG. 7A, except that in step 155 of this embodiment, full charging power is provided to the external battery 64, while the implant battery 86 is simultaneously weakly charged. Full charging of the external battery 64 occurs as before, by enabling battery charging circuit 62 to provide full charging power Ibat(max) to the external battery 64.

Figure 8B:
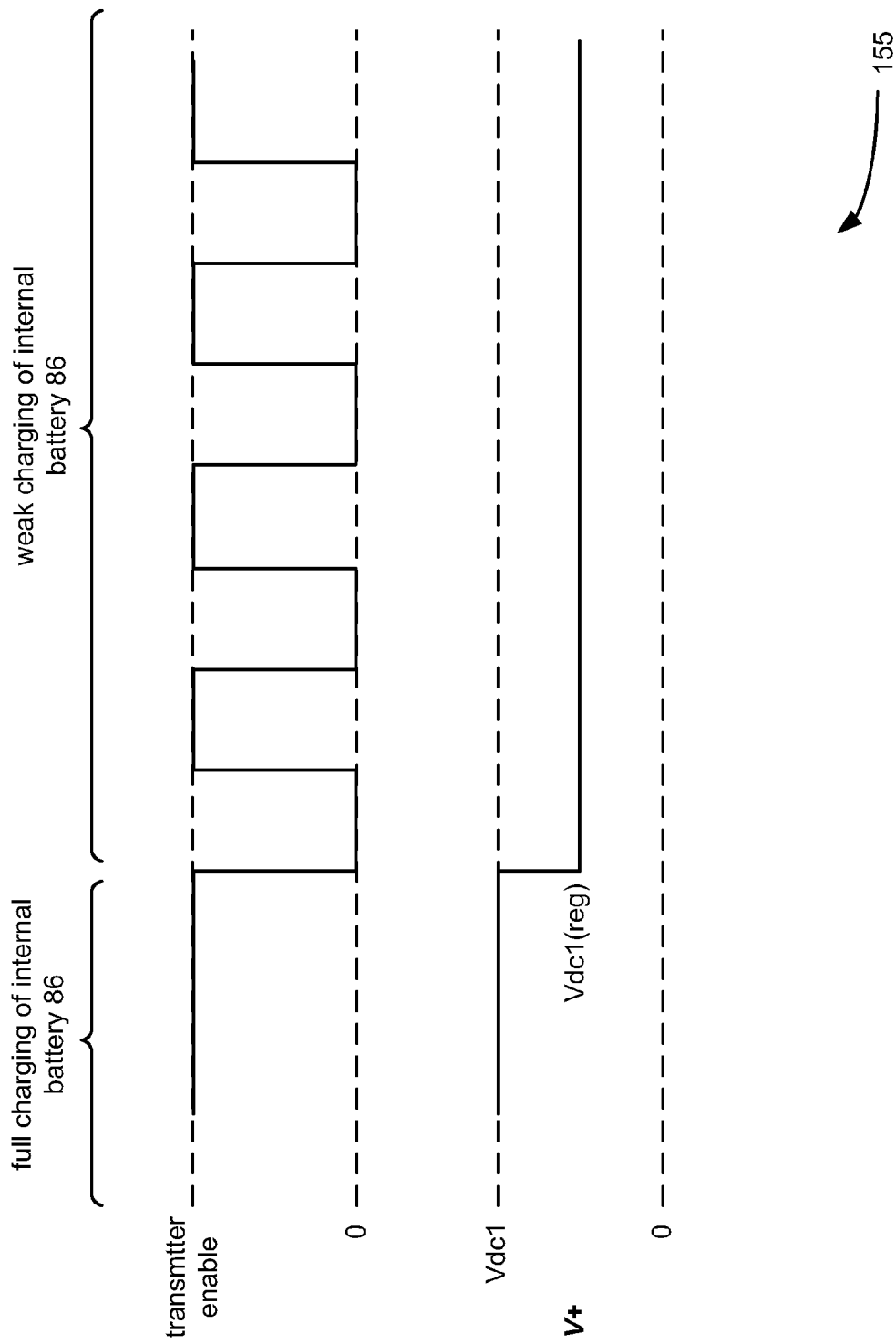

By contrast, less than full power levels, at least on average, is provided to the transmitter 68 to provide a less-than-full-power magnetic charging field, which in turn charges the implant battery 86 to a lesser extent. A couple of ways for achieving a lower power draw in the transmitter 68 are shown in FIG. 8B. In the first way illustrated at the top of FIG. 8B, the transmitter is selectively enabled and disabled (i.e., duty cycled), such that it produces a full strength magnetic charging field at some times, but at other times is off. In the second way illustrated in FIG. 8B, the power supply for the tank circuit in the transmitter 68, V+ (see FIG. 3B), is lowered from Vdc1 (the voltage normally used by the transmitter if the external battery 64 is not sufficiently charged) to Vdc1(ref), which comprises a stepped-down voltage produced by optional regulator 98 as shown in FIG. 3A. In either case, on average, the average power level of the transmitter 68 is lessened compared to when the implant battery is charged by itself, as is the magnitude of the resulting magnetic charging field.

During simultaneous charging of the external battery 64 and the implant battery 86 in step 155, the capacities of these batteries are periodically checked. If neither is fully charged, the simultaneous charging continues. If one of the batteries is charged first, then further charging of that batteries ceases and charging of the other battery occurs as normal. As these latter steps in 150 are the same as was described with respect to steps 140 in FIG. 7A, they are not again repeated.

Regardless of whether the embodiment of FIG. 7A or 8A is considered, simultaneous charging occurs, but with reduced power draw by either the battery charging circuit 62 or the transmitter 68. As both of these components have been noticed as significant in generating heat in the coil controller 24, mitigating the power draw in at least one of these components helps to address the heat problem created by the need to charge both the external battery 64 and the implant battery 86, thus providing a safer solution.

Figure 9:
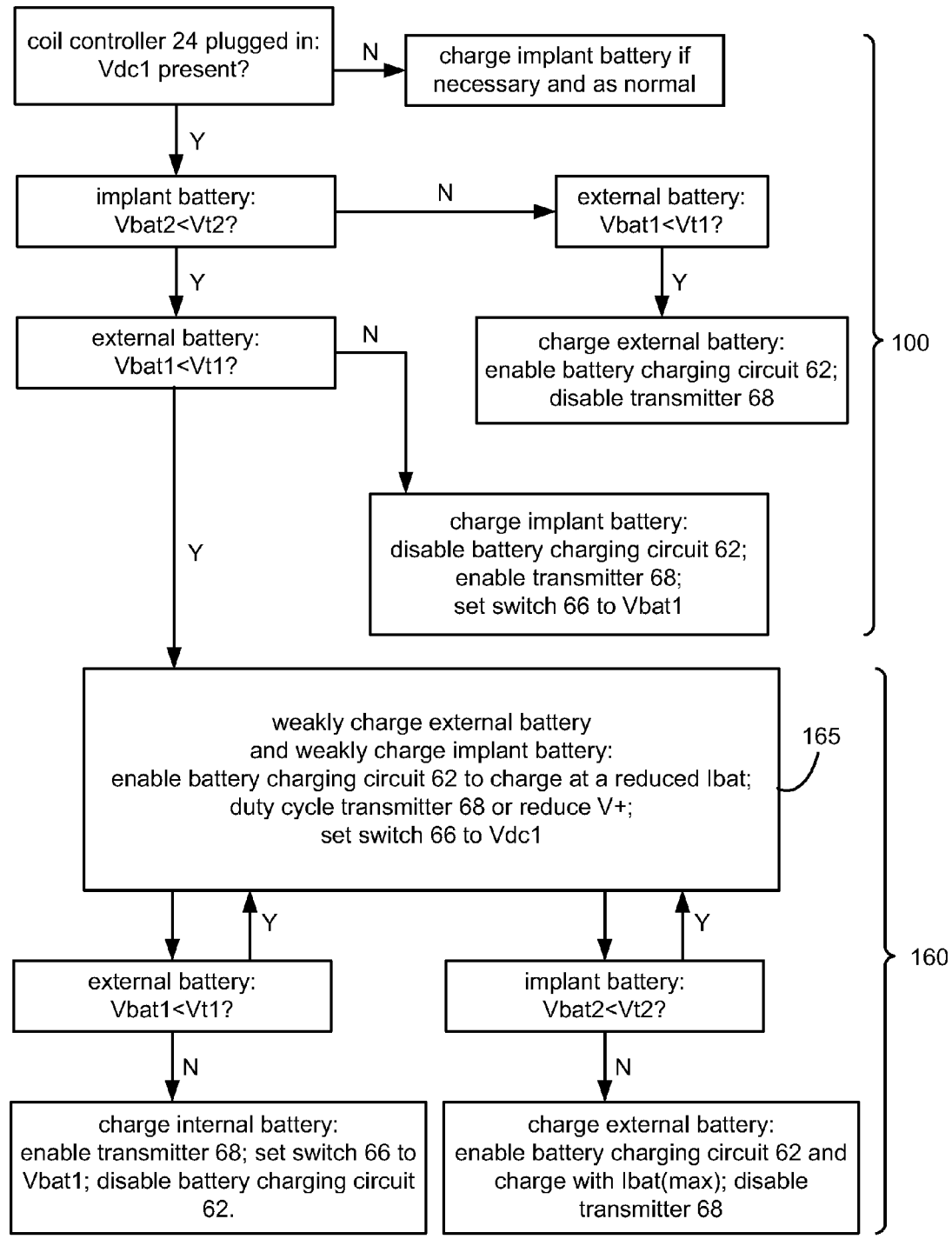
FIG. 9 illustrates a charging algorithm that allows for simultaneous charging of the external and implant batteries, but with both being only weakly charged at low power.

FIG. 9 comprises an approach similar to those of FIGS. 7A and 8A in that it allows simultaneous charging of both the external battery 64 and the implant battery 86, but such charging occurs by weakly charging both of these batteries simultaneously. Therefore, as shown in step 165, should both batteries need charging, the external battery 64 is charged with a reduced power draw in the battery charging circuit 62 (e.g., with a lower average Ibat as shown in FIG. 7B) and the internal battery 86 is charged using a lower power draw at the transmitter 68 (e.g., as shown in FIG. 8B). Once either battery 64 or 86 is fully charged, then the other can be charged at full power levels, as discussed earlier. Thus, the embodiment of FIG. 9 would cut power draw in both the battery charging circuitry 62 and the transmitter 68 simultaneously, even further lowering the risk (when compared to FIGS. 7A and 8A) that simultaneous activation of these circuits would cause overheating of the coil controller 24.

Figure 10:
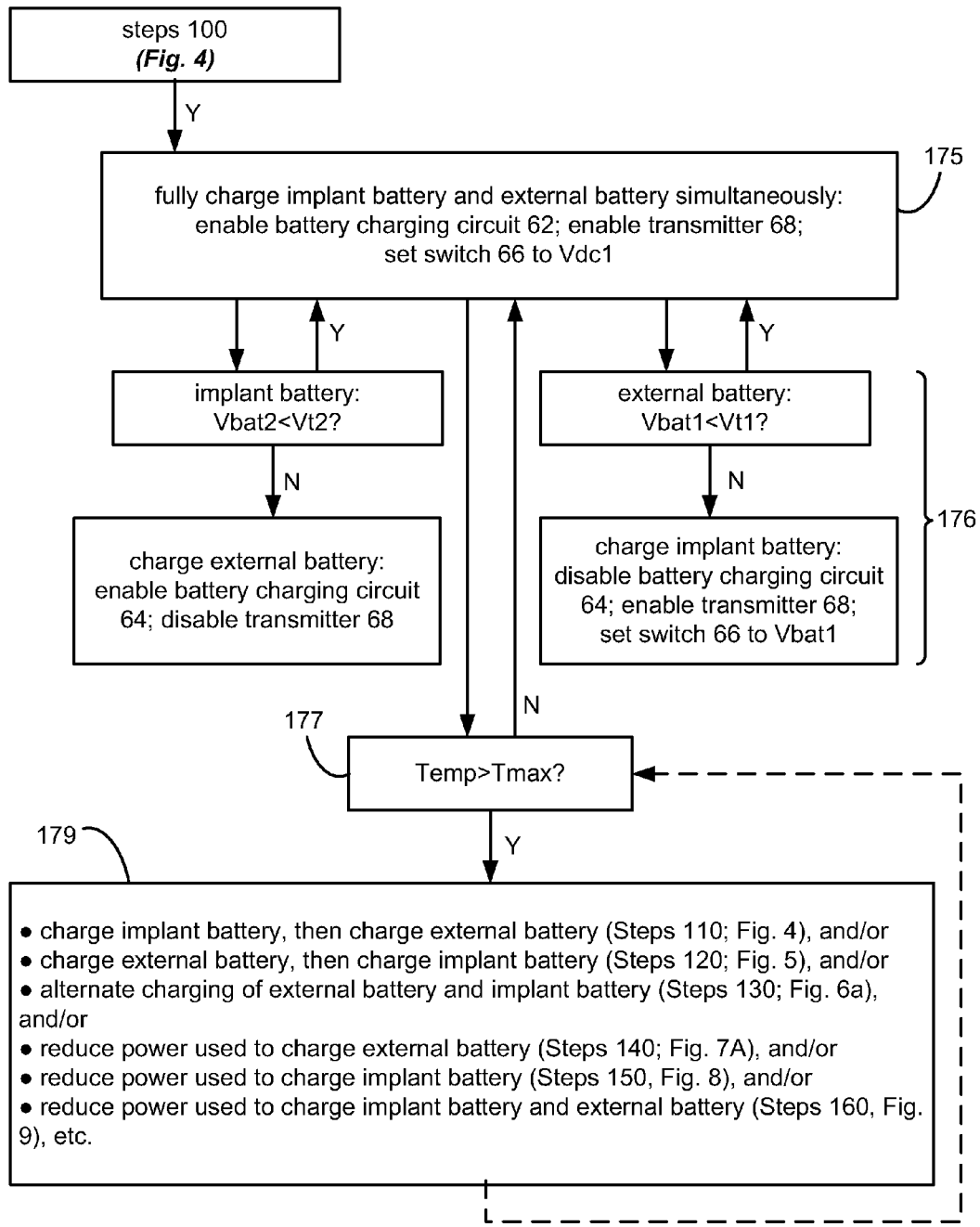
FIGS. 10 and 11 illustrates charging algorithms that change to reduce heat generation depending on the temperature sensed in the external charging components.

FIG. 10 provides yet other embodiments for a charging algorithm for charging both the external battery 64 in the coil controller 24 and the implant battery 86 in the microstimulator 10. As already mentioned, the inventors have noted that simultaneous activation of the battery charging circuit 62 and the transmitter 68 raises concerns about heat generation in the coil control 24. Accordingly, the embodiment of FIG. 10 factors consideration of the actual temperature of the coil controller 24 into consideration when controlling the charging of both batteries. Thus, and referring to FIG. 3A, optional temperature sensor(s) 69 is provided in the coil controller 24, which provide information concerning the temperature, T, to the microcontroller 60. If a plurality of temperature sensors 69 are used, the indicated temperature T can comprise an average of temperature sensed by each sensor 69 for example. Temperature sensor(s) 69 can comprise thermocouples, thermistors, or the like, and can be affixed at any location in or on the housing 27 of the coil controller 24.

After initial steps 100 during which it is concluded that both external battery 64 and implant battery 86 require charging, step 175 allows both of these batteries to be fully charged at maximum power levels. This entails enabling the battery charging circuit 62, enabling the transmitter 68, and setting switch 66 to Vdc1. By this configuration, Vdc1, the power provided by the plug 26, simultaneously fully charges the external battery 64 and powers the transmitter 68 for full powering of the implant battery 86.

As full power level charging of both batteries 64 and 86 progresses as provided in step 175, three conditions are continually monitored, logically on a periodic basis: the capacity of batteries 64 and 86 in steps 176, and the temperature of the coil controller 24 in step 177. Monitoring the capacities of the batteries in steps 176 is similar to steps 147 and 157 in FIGS. 7A and 8A respectively, and thus are not further discussed. However, step 177 provides a significant difference from earlier embodiments, because it ascertains whether the temperature of the coil controller 24 is higher than a predetermined temperature, Tmax. Tmax may represent a maximum safe temperature as determined by the designer of the external charging components 20. For example, Tmax may comprise 41° C., as temperatures above this limit may have the ability to hurt a patient after prolong contact.

Should the temperature exceed this safe value Tmax in step 177, then, and as shown in step 179, charging of the batteries 64 and 86 can be modified so that both batteries 64 and 86 are not simultaneously charged, or not simultaneously charged to a full extent. This can comprise employing any of the heat-reducing charging techniques previously disclosed in FIGS. 4-9 for example. Thus, in step 179: the implant battery can be charged, followed by charging of the external battery (Steps 110; FIG. 4), and/or: the external battery can be charged, followed by charging of the implant battery (Steps 120; FIG. 5), and/or; the external battery and implant battery can be charged in alternative fashion (Steps 130; FIG. 6A), and/or; the power used to charge external battery can be reduced (Steps 140; FIG. 7A), and/or; the power used to charge implant battery can be reduced (Steps 150, FIG. 8), and/or; the power used to charge implant battery and external battery can be reduced (Steps 160, FIG. 9), etc.

Implementation of the heat-reducing charging techniques in step 179 would be expected to lower the temperature of the coil controller 24 when compared to full-blown simultaneous charging of the external 64 and implant 86 batteries (step 175). Accordingly, as an optional step in the process depicted in FIG. 10, should the temperature of the coil controller 24 once again fall below Tmax (Temp<Tmax; see step 177), then simultaneous full charging of both batteries 64 and 86 can once again commence. If not, then at least one temperature mitigation technique of step 179 continues to operate. However, this is optional, and instead, once Tmax is exceeded, the charging system can be constrained by the temperature mitigating techniques of step 179, without return to full blown charging of both batteries as in step 175.

To summarize, the charging algorithm of FIG. 10 allows both batteries 64 and 86 to be charged at full power (step 175), until the temperature of the coil controller 24 exceeds a maximum safe temperature, Tmax (step 177). Once this temperature is exceeded, the microcontroller 60 employs a temperature-reducing scheme (step 179) designed to not simultaneously charge both batteries 64 and 86, at least to a full extent. Once the temperature of the coil controller 24 cools (Temp<Tmax) (step 177) then full charging of both batteries 64 and 86 can once again continue if desired.

Figure 11:
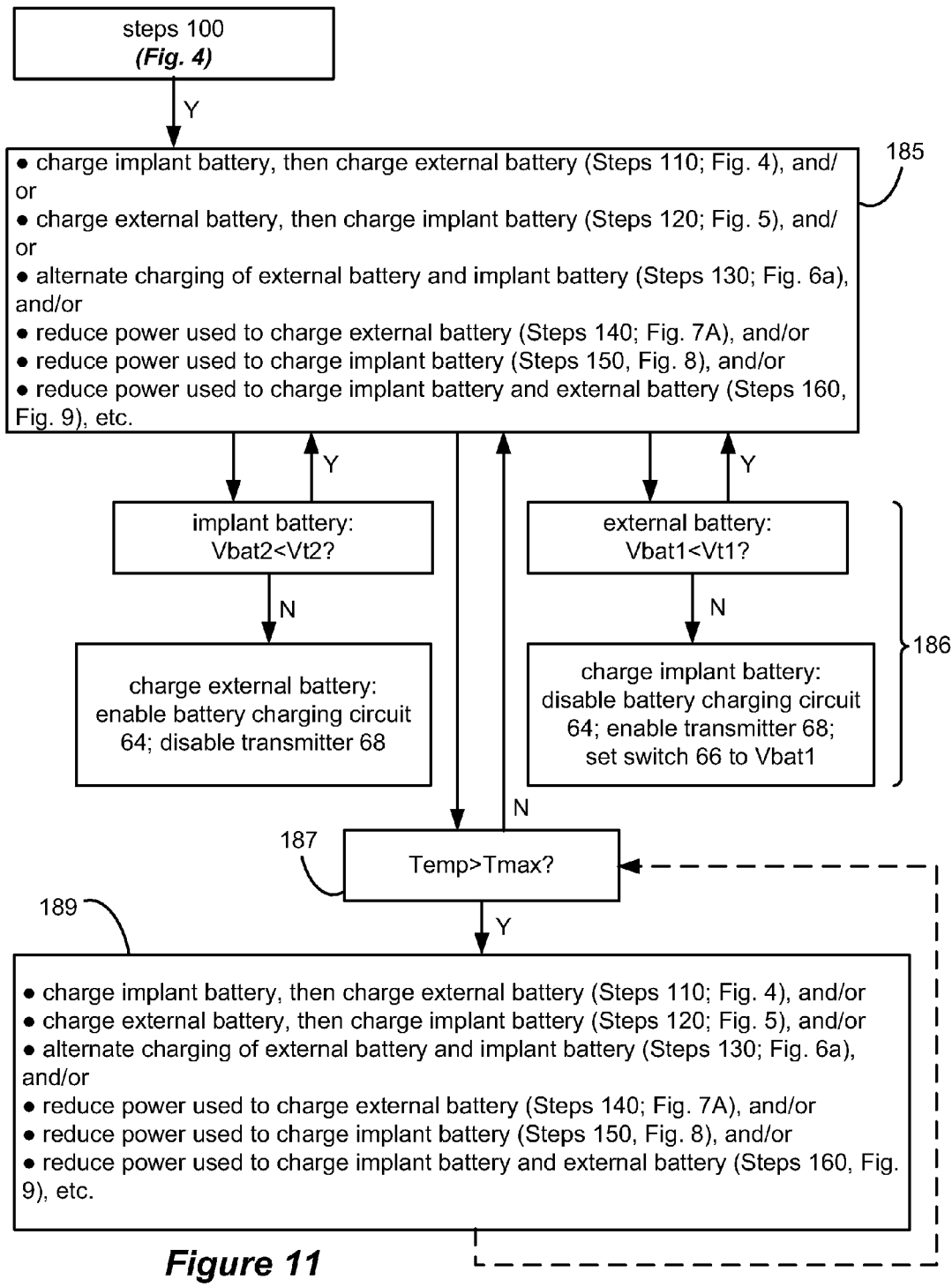

FIG. 11, like FIG. 10, also controls the charging algorithm in accordance with the temperature of the coil controller 24. However, in constant to step 157 in FIG. 10 which allows for simultaneous full charging of the both the external battery 64 and the implant battery 86, step 185 in FIG. 11 only allows a temperature-reducing scheme to be used. This step 185 can comprise use of any of the techniques discussed earlier in FIGS. 4-9 or combinations thereof. After implementation of a particular temperature-reducing scheme in step 185, the temperature of the coil controller 24 is monitored (step 187). Should the temperature rise above a safe temperate (Tmax), which might indicate that the chosen temperature-reducing scheme in step 185 is insufficient, a different temperature-reducing scheme (e.g., another of the techniques from FIGS. 4-9) can again be tried in step 189. In other words, a first algorithm for charging both batteries is used first (185) followed by a second algorithm for charging both batteries (187) should the temperature become too high.

Although disclosed in the context of a multi-electrode microstimulator, it should be understood that the disclosed battery charging techniques can have applicability to many other sorts of implantable medical device system applications, including, drug pumps, cochlear implants, pacemakers, etc.

It should be noted that the control circuitry, e.g., microcontroller 60 (e.g., FIG. 3A) can comprise any number of logic circuits, which circuits can be discrete and coupled together, or which can be integrated in a traditional discrete microcontroller circuit. Either way, "circuitry in the external charger" as used in the claims should be construed as covering circuitry embodied in a microcontroller or a microprocessor, or any other arrangement of logical circuit(s), whether integrated or not, for performing the necessary control functions required by the claims. Moreover, "circuitry in the external charger" as used in the claims can be the same or different from other circuits recited as being "circuitry in the external charger" depending on context and on the control functions as recited by the claims.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method for charging an implant battery in an implantable medical device and an external battery in an external charger, comprising:
   using circuitry in the external charger to determine that both the external battery in the external charging device and the implant battery in the implantable medical device require charging;
   if it is determined that both the external battery and the implant battery require charging, using circuitry in the external charger to enable charging a first battery comprising either the external battery or the implant battery while disabling charging of a second battery comprising the other of the external battery or the implant battery; and
   upon determining using circuitry in the external charger that the first battery is charged to a pre-determined level, using circuitry in the external charger to disable charging of the first battery while enabling charging of the second battery.

2. The method of claim 1, wherein charging the external battery is enabled or disabled by enabling or disabling a battery charging circuit in the external charger.

3. The method of claim 1, wherein charging the implant battery is enabled or disabled by enabling or disabling a wireless transmitter in the external charger which provides wireless power to the implant battery.

4. The method of claim 1, wherein the circuitry in the external charger comprises a microcontroller.

5. The method of claim 1, wherein the predetermined level comprises a voltage for the battery being charged.

6. The method of claim 1, wherein determining that the implant battery requires charging requires telemetry of an implant battery voltage from the implantable medical device to the external device.

7. A method for charging an implant battery in an implantable medical device and an external battery in an external charger, comprising:
   using circuitry in the external charger to determine that both the external battery in the external charging device and the implant battery in the implantable medical device require charging; and
   if it is determined that both the external battery and the implant battery require charging, using circuitry in the external charger alternate between charging of the external battery and the implant battery.

8. The method of claim 7, wherein the external battery is charged for a first time period, and wherein the implant battery is charged for a second time period.

9. The method of claims 8, wherein the first and second time periods are equal.

10. The method of claim 7, wherein both the external battery and implant battery are charged using a DC voltage derived from an AC power source.

11. The method of claim 7, further comprising upon determining using circuitry in the external charger that one of the external battery or the implant battery is charged, using circuitry in the external charger to enable charging of the other of the external battery of the implant battery while disabling charging of the charged battery.

12. The method of claim 7, wherein the implant battery is charged using a wireless transmitter in the external charger.

13. A method for charging an implant battery in an implantable medical device and an external battery in an external charger, comprising:
   using circuitry in the external charger to determine that both the external battery in the external charging device and the implant battery in the implantable medical device require charging; and
   if it is determined that both the external battery and the implant battery require charging, using circuitry in the external charger to control the external charger to simultaneously charge the external battery and the implant battery, wherein the external charger controls charging of either or both of the external battery and the implant battery at a lower average power level than would be used were either battery to be charged by itself.

14. The method of claim 13, wherein the external battery is charged at a lower average power level.

15. The method of claim 14, wherein the external battery is charged at a lower average power level by reducing its average charging current.

16. The method of claims 15, wherein the reduced average charging current comprises a constant current less than a constant current that would be used to charge the external battery without simultaneous charging of the implant battery.

17. The method of claim 15, wherein the reduced average charging current comprises a time varying current which on average is lower than a current which that would be used to charge the external battery without simultaneous charting of the implant battery.

18. The method of claim 13, wherein the internal battery is charged at a lower average power level.

19. The method of claim 18, wherein the internal battery is charged by activating a wireless transmitter within the external charger, and wherein the transmitter is powered at a lower average power level by using a power supply voltage less than a the power supply voltage that would be used without simultaneous charging of the external battery.

20. The method of claim 13, wherein the internal battery is charged by activating a wireless transmitter within the external charger, and wherein the transmitter is powered at a lower average power level by duty cycling the transmitter.

21. A method for charging an implant battery in an implantable medical device and an external battery in an external charger, comprising:
   using circuitry in the external charger to determine that both the external battery in the external charging device and the implant battery in the implantable medical device require charging; and
   if it is determined that both the external battery and the implant battery require charging, using circuitry in the external charger to simultaneously charge the external battery and the implant battery at full power levels;
   using circuitry in the external charger to assess a temperature of the external charger;
   if the assessed temperature exceeds a predetermined temperature, using circuitry in the external charger to charge one or both of the external battery or the implant battery at less than their full power levels.

22. The method of claim 21, wherein the full power levels comprises power levels at which the external battery or the implant battery would be individually charged were the other battery not being simultaenously charged.

23. The method of claim 21, wherein lowering the power level comprises lowering the power supply voltage of a transmitter in the external charger which wirelessly provides power to the implant battery, or comprises lowering a power supply voltage used to charge the external battery.

24. A method for charging an implant battery in an implantable medical device and an external battery in an external charger, comprising:
   using circuitry in the external charger to determine that both the external battery in the external charging device and the implant battery in the implantable medical device require charging; and
   if it is determined that both the external battery and the implant battery require charging, activating a first algorithm in the external charger for charging the external battery and the implant battery;
   using circuitry in the external charger to assess a temperature of the external charger;
   if the assessed temperature exceeds a predetermined temperature, activating a second algorithm in the external charger for charging the external battery and the implant battery.

25. The method of claim 24, wherein the first algorithm comprises charging the external battery and implant battery simultaneously, but wherein the second algorithm does not charge the external battery and the implant battery simultaneously.

26. The method of claim 25, wherein the first algorithm charges the external battery and the implant battery at a combined first power levels, but wherein the second algorithm charges the external battery and the implant battery at a combined second power level less than the first power level.

27. The method of claim 24, further comprising
   using circuitry in the external charger to assess a temperature of the external charger after activation of the second algorithm;
   if the assessed temperature is below the predetermined temperature, activating the first algorithm.

* * * * *